United States Patent [19]

Lasco

[11] 3,947,521

[45] Mar. 30, 1976

[54] OXIDATION OF ALLYLACETONE TO 2,5-HEXANEDIONE

[75] Inventor: Ralph H. Lasco, Painesville, Ohio

[73] Assignee: Diamond Shamrock Corporation, Cleveland, Ohio

[22] Filed: Apr. 8, 1974

[21] Appl. No.: 458,475

[52] U.S. Cl. .................................... 260/593 R
[51] Int. Cl.² ....................................... C07C 45/00
[58] Field of Search ................. 260/597 B, 593 R

[56] References Cited
UNITED STATES PATENTS

| | | |
|---|---|---|
| 3,301,905 | 1/1967 | Rumenschneider et al..... 260/597 B |
| 3,303,020 | 2/1967 | Clement et al................. 260/597 B |
| 3,701,810 | 10/1972 | Hasegawa et al. ............. 260/597 B |

FOREIGN PATENTS OR APPLICATIONS

| | | |
|---|---|---|
| 47-11411 | 4/1972 | Japan................................ 260/577 |

OTHER PUBLICATIONS

Yamamota et al., Kogyo Kakaku Zasshi, Vol. 71, (6) pp. 945–946, (1968).
Smidt et al., Angervandte Chem., Vol. 71 (5), pp. 176–182, (1959).

Primary Examiner—Bernard Helfin
Assistant Examiner—James H. Reamer
Attorney, Agent, or Firm—Helen P. Brush

[57] ABSTRACT

An economical process is described for the oxidation of allylacetone to 2,5-hexanedione in a mixed solvent system, using palladium chloride catalyst in the presence of copper chloride and oxygen. Through the use of high copper/palladium mole ratios together with copper/allylacetone mole ratios greater than 1, high yields of product are obtained with minimal losses of palladium.

6 Claims, No Drawings

OXIDATION OF ALLYLACETONE TO 2,5-HEXANEDIONE

BACKGROUND OF THE INVENTION

1. Field of the Invention

This invention relates to a commercial process for the preparation of 2,5-hexanedione, i.e., acetonylacetone, from allylacetone and more particularly relates to the oxidation of allylacetone using palladium chloride as the catalyst in the presence of copper chloride and oxygen to prepare high yields of 2,5-hexanedione with only small losses of the palladium catalyst.

2. Description of the Prior Art 2,5-Hexanedione or acetonylacetone is important as an organic chemical intermediate. Preparation of this compound through various synthesis routes has been reported in the prior art. For example, Adams et al. in J. Am. Chem. Soc., Vol. 72, p 4368 (1950) describe the synthesis of 2,5-hexanedione by condensing propylene oxide with acetoacetic acid esters to produce alpha-aceto-gamma-valerolactone, which, in turn, is reacted with dilute hydrochloric acid and converted into 5-hydroxy-2-hexanone. To obtain 2,5-hexanedione, the hydroxy-hexanedione product is then oxidized together with sodium dichromate and sulfuric acid. Also, Shenk in Ber., Vol. 77, p 661 (1944) describes the preparation of 2,5-hexanedione by oxidizing 2,5-dimethylfuran to 3-hexene-2,5-dione, which product then is hydrogenated to produce 2,5-hexanedione. Still further, in U.S. Pat. No. 2,525,672, Heilbron et al. describe the preparation of 2,5-hexanedione by first reacting 1-bromo-2,3-epoxybutane with monosodium acetylide in liquid ammonia, and then reacting the 3-hexene-5-yn-2-ol product obtained with mercury sulfate and sulfuric acid.

For one or more reasons, however, all of these prior art processes are disadvantageous for preparing 2,5-hexanedione conveniently and economically. The process of Adams et al is a multistage process which provides only low yields of product. The Shenk process, besides providing only moderate yields of product, utilizes 2,5-dimethylfuran which is obtained only with difficulty. The Heilbron et al process likewise utilizes reactants which are difficult to handle and only moderate product yields are realized.

More recently, in Kogyo Kaguku Zasshi 71, (6), p 945-6 (1968) as well as in Japanese Patent Publication No. 1972–11411, Takamori Konaka and Sadao Yamamoto have described a simplified, one-step process for producing good commercial yields of 2,5-hexanedione from allylacetone in a mixed solvent system composed of water and either benzene or dimethylformamide. In this process, palladium chloride is employed as the oxidation catalyst in the presence of prescribed amounts of cupric chloride and oxygen. The process is carried out at temperatures ranging usually from 60°–80°C for an overall time period ranging generally from 3 to 12 hours but typically from 7 to 12 hours. Upon completion of the reaction, the 2,5-hexanedione product is reported to be easily recoverable from the reaction mixture and purified. However, from practice of this process, substantial quantities of undesirable byproducts are formed and losses of the expensive palladium chloride catalyst component are found to be substantial.

It has now been found that by conducting the oxidation process in a manner similar to that described by Konaka and Yamamoto, but with the use of much greater copper/palladium mole ratios and copper/allylacetone mole ratios than previously employed, commercially attractive yields, i.e., greater than about 70%, by weight of theoretical, of 2,5-hexanedione product can be obtained in significantly shorter reaction times. Most important, practice of this process results in much reduced losses of the expensive palladium catalyst.

SUMMARY OF THE INVENTION

Accordingly, the present invention relates to an improved process for oxidizing allylacetone (or ALA) in high overall conversions and with high selectivity to 2,5-hexanedione (or HDO). Carried out in a mixed solvent system composed of water with either benzene or dimethylformamide, this process utilizes palladium chloride as the oxidation catalyst in the presence of oxygen and either cupric chloride or mixtures of cupric and cuprous chlorides as the reoxidizing agents for the palladium, the copper/palladium mole ratios employed ranging generally from 20 to 150:1. Also, the minimum mole ratio of total copper to the ALA reactant employed is greater than 1. Under optimum conditions in practice of this process, palladium losses may be reduced to about 2 cents per pound of HDO product, based on a palladium chloride cost of $333/pound.

DESCRIPTION OF THE PREFERRED EMBODIMENTS

The oxidation of allylacetone (ALA) to 2,5-hexanedione (HDO) together with the secondary oxidation-reduction reactions occurring in the process of the instant invention may be broadly represented by the following equations:

1. Oxidation of allylacetone to 2,5-hexanedione:

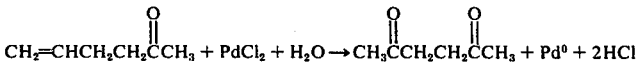

2. Regeneration of palladium to catalytic palladium chloride:

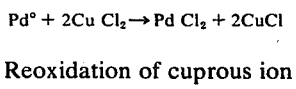

3. Reoxidation of cuprous ion to cupric ion:

As illustrated in Equation (1) above, the palladium chloride catalyst is reduced to palladium metal during the oxidation of the ALA. The metal is rapidly regenerated for reuse again as catalytic palladium chloride by the oxidizing action of the cupric chloride, as set forth in Equation (2). In turn, the cuprous chloride formed from the palladium reoxidation step is reoxidized to cupric chloride in the presence of oxygen and hydrochloric acid (Equation 3).

The ALA which is oxidized in the process of this invention is a commercially-available compound which may be synthesized by various methods. For example, it may be prepared from allyl chloride and ethyl acetoacetate as described by Schecter et al, J. Am. Chem. Soc., 71, p 3165 (1949). It likewise may be synthesized by reacting allyl alcohol and acetone in the presence of an acid-acting catalyst as set forth in U.S. Pat. No. 3,114,772, issued Dec. 17, 1963. Neither the ALA reactant per se nor any particular synthesis method therefor constitute a part of the present invention.

The process of this invention utilizes as the oxidation catalyst system, palladium chloride and cupric chloride or, alternatively, mixtures of cupric and cuprous chlorides, in proportions which provide much higher copper/palladium mole ratios than heretofore reported.

It is believed that use of high copper/palladium mole ratios herein either inhibits the conversion of ALA to undesirable byproducts, e.g., $\pi$-allyls or else further converts any such products which may form to other compounds which, unlike $\pi$-allyls, do not form solid, difficultly soluble and stable complexes with palladium, thereby rendering this metal catalytically useless for further reaction.

From 20–150 moles of copper chloride per each mole of palladium chloride generally may be suitably used. More advantageous are ratios of 22–100 moles of copper chloride per mole of palladium chloride, with ratios of 22–50 moles of copper chloride/mole of palladium chloride being especially advantageous and presently preferred.

The copper chloride requirement itself may be supplied by using either cupric chloride ($CuCl_2$) alone, or a mixture thereof with cuprous chloride ($CuCl$). Use of the mixed copper salts has been found to be advantageous for attaining optimum reaction rates. In such instances, the proportion of CuCl employed typically will be less than 50 weight percent of the mixture.

To obtain the improved process results described herein, it has been found necessary to employ, in addition to the aforedescribed copper chloride/palladium chloride ratios, a sufficient amount of copper chloride to provide a copper/ALA mole ratio which is greater than 1, at least in the initial stages of the oxidation reaction.

As shown in the above Equation (1), hydrochloric acid is produced as a byproduct in the initial oxidation reaction. In prior art practice it has been customary to incorporate additional acid into the reaction to assure best results. In the process of this invention, however, no hydrochloric acid usually needs to be incorporated into the initial reaction mixture, since the amount of copper chloride employed will generate sufficient quantities of hydrogen and chloride ions to facilitate reoxidation of the palladium. In this manner, the reaction mixture can be easily controlled at a pH of 1.0–3.0, depending upon the amount of oxygen available in the system. It should also be noted that greater yields of HDO product typically can be obtained in faster reaction times under similar reaction conditions, if no acid is added.

The purity of the ALA reactant is not highly critical for obtaining optimum yields of the product. In general, however, it is desirable to employ ALA which is at least and preferably more than 93% pure.

Oxygen may be introduced into the reaction in finely dispersed form at a prescribed rate or the reaction alternatively may be run under oxygen pressure. For example, a satisfactory rate of oxygen feed at atmospheric pressure typically is a minimum of about 2000 cc/min/liter of aqueous oxidant solution. Particularly advantageous results are obtained applying oxygen at a rate of 4,000–10,000 cc/min/liter of aqueous oxidant solution. In pressurized reactions, a satisfactory minimum oxygen feed rate is about 50 cc/min/liter of the oxidant solution.

As previously described, the solvent system employed herein is a mixture of water with either benzene or dimethylformamide. When employing the heterogeneous benzene-water system, from 1 to 2 parts benzene, by volume, are advantageously used for each part of water. If using the homogeneous dimethylformamide-water system, from 2 to 8 parts of solvent, by volume, generally are used for each part of water. Whichever solvent system is employed, from 2 to 5 parts of said system, by volume, typically are used for each part of ALA reactant.

In general, the process may be suitably carried out at temperatures ranging from 35° to 100° C. Reaction temperatures of 40°–80° C are more advantageous and temperatures of 60°–80° C are most preferred at present. Further, in reactions which employ the benzene-water solvent system, a suitable reaction temperature at atmospheric pressure is approximately 67° C, i.e., the reflux temperature of the benzene-water azeotrope. If higher reaction temperatures are desired for such reactions, these must, of course, be pressurized.

Reaction times herein may range generally from 30 minutes to 6 hours, with times ranging from 30 minutes to 3 hours being especially suitable and presently preferred.

According to one embodiment, the process of this invention generally may be carried out by successively charging the prescribed quantities of palladium chloride, copper chloride, water, and organic solvent together with the total charge of ALA into a reactor fitted with an agitator, thermometer, condenser, and an oxygen sparger. With continued agitation, oxygen is then introduced into the system and the reaction mixture is heated to the desired temperature. The reaction is continued at this temperature until 80% or more of the ALA has been converted (as determined by analysis of an aliquot sample via gas phase chromatography).

Alternatively, the process may be conducted by initially charging the prescribed quantities of catalyst and solvent components and only a portion of the ALA reactant into the reactor as described above, while subsequently feeding the remaining ALA requirement into the reactor at a prescribed rate throughout the reaction. In still another method, all of the ALA requirement may be fed incrementally at a prescribed rate throughout the reaction. Further, it is to be understood that any of the various modes for carrying out the process may be conducted efficiently either at atmospheric conditions or under oxygen pressure.

Upon completion of the reaction, whichever procedure is employed, the HDO product is separated and purified by fractionation, selective extraction, distillation, and the like. For example, when the heterogeneous benzene-water system is employed, the benzene and water layers will easily separate. The major amount of product is contained in the benzene layer and the product may be reclaimed therefrom by solvent-stripping. The aqueous layer may be extracted with benzene to recover small quantities of product present therein.

When the homogeneous dimethylformamide-water system is employed, the product can be reclaimed from the one-phase reaction mixture by selective extraction using hydrocarbons which are essentially immiscible with water, e.g., pentane, hexane, heptane, and the like.

The amount of palladium lost in the reaction, which amount will be contained in the product stream as, e.g., the benzene fraction, can be easily determined by analysis. In preferred embodiments of the process, as will be shown hereinafter by a specific example, the amount of palladium lost per reaction may be as little as 2 cents/pound of product, based on a palladium chloride cost of $333/pound.

After separation, the aqueous layer (containing the palladium catalyst) can be recycled to the reactor along with fresh ALA and solvent, and the process of this invention may be repeated in a somewhat semicontinuous manner. Prior to recycling, however, the aqueous layer need not be stripped of product, as the HDO can be recovered substantially after the next cycle. Even if present in the reaction mixture at the start of oxidation, the HDO will not react further to more complex derivatives, e.g., triketones, furans, etc., nor will it form chlorinated byproducts.

In order that those skilled in the art may more completely understand the present invention and the preferred methods by which it may be carried out, the following specific examples are given. In these examples and elsewhere herein, where proportions of ingredients may be given in parts, such proportions are by weight, unless otherwise indicated.

EXAMPLE 1

Experiment A

ALA was oxidized in a benzene-water solvent system according to the teachings of Konaka and Yamamoto, employing mole ratios of cupric chloride/palladium chloride and of cupric chloride/ALA as set forth in Japanese Patent Publication No. 1972-11411. A 500-cc flask fitted with a thermometer, agitator, condenser, and oxygen sparger was charged successively with 100 cc water, 150 cc benzene, 35 cc (0.286 mole) of ALA assaying 95.5%, 16.1 g of cupric chloride, and 5.3 g palladium chloride. Five cc hydrochloric acid (HCl) was then added. The mole ratio of cupric chloride/palladium chloride was 4:1, and the ratio of cupric chloride/ALA was 0.42. With continued agitation, the reaction mixture was heated to 67° C under atmospheric conditions while feeding oxygen at a rate of 200 cc/min. Heating was continued at this temperature for 7.5 hours.

Agitation was then discontinued and the reaction mixture was cooled. Two liquid layers developed in the reaction mixture along with a yellow solid which prevented sharp phase separation. Filtration of the reaction mixture to remove the yellow organopalladium compound was necessary in order that the benzene product phase could be separated from the aqueous catalyst phase. The separated aqueous phase was extracted with three 150 cc portions of benzene to recover the HDO which was soluble in the catalyst solution. Both the main benzene-HDO layer and the combined washings were analyzed for palladium. In addition, the palladium content of the $\pi$-allyl compound was determined. Conversion of the ALA and yield of HDO was determined by gas phase chromatography of the benzene solution with the results obtained shown in the table below.

Experiment B

The aforedescribed reaction was repeated, except that no HCl was incorporated in the reaction mixture and the reaction was conducted at 67° C for 2 hours. Upon standing, the reaction mixture separated into two liquid phases containing a large amount of solid. Isolation and recovery of the 2,5-hexanedione product solution and analysis of this solution were as described previously with the results obtained shown in the following table.

Experiment C

The reaction described in A above was again repeated, employing, in this instance, 53.0 g cupric chloride and 5.3 g palladium chloride, whereby the ratio of copper chloride/palladium chloride was 13:1 and the cupric chloride/ALA ratio was 1.3. As in Experiment A, 5 cc HCl was incorporated into the reaction mixture.

This reaction was conducted at 67° C for 5.5 hours. Upon completion of the reaction, the reaction mixture separated into two liquid phases upon standing. No solids were observed. Isolation and recovery of the product were as previously described with the results obtained listed as follows:

TABLE 1

| Example | Mole Ratio Cu/Pd | Mole Ratio Cu/ALA | % ALA Conversion | % HDO Selectivity | % HDO Yield | Pd Loss cent/lb HDO |
|---------|------------------|-------------------|------------------|-------------------|-------------|---------------------|
| 1A      | 4                | 0.42              | 87               | 71                | 62          | 810                 |
| 1B*     | 4                | 0.42              | 96               | 59                | 57          | 4219                |
| 1C      | 13               | 1.3               | 100              | 54                | 54          | 14                  |

*No HCl incorporated in the reaction mixture.

As the results of Experiments 1A and 1B indicate, the oxidation of ALA utilizing cupric chloride/palladium chloride mole ratios and cupric chloride/ALA mole ratios as set forth in the aforesaid Japanese patent teachings, whether or not conducted with the addition of HCl, gave only moderate yields of HDO with very high losses of palladium. the palladium loss was exceptionally high from the experiment with no incorporated HCl. Further, from each experiment, a sizeable quantity of a solid, undesirable byproduct was obtained, although ALA conversion was good. The formation of this material reduced the yield of the desired ketone product.

Experiment 1C was conducted utilizing a cupric chloride/ALA mole ratio according to the process of this invention rather than as taught in the prior Japanese patent teaching. In this manner, formation of a solid undesirable product was prevented and the palladium loss was greatly reduced. However, by using a cupric chloride/palladium chloride mole ratio within the range taught by the prior art and also by incorporating HCl into the reaction mixture, a sizeable quantity of a soluble, chlorinated byproduct was produced. The selectivity to 2,5-hexanedione and the yield of this product was thus markedly reduced.

EXAMPLES 2–5

A series of experiments illustrating the process of this invention are as follows:

For each experiment, a 500-cc flask fitted as described previously is successively charged with 100 cc water, 150 cc benzene, 20 cc (0.163 mole) of ALA (95.5% assay) and amounts of cupric chloride and palladium chloride to provide copper/palladium (Cu/Pd) mole ratios as shown in the following table. For example, use of 30.0 g (0.223 mole) cupric chloride and 1.6 g (0.009 mole) palladium chloride provides a copper/palladium mole ratio of approximately 25:1; and the copper/ALA mole ratio will be about 1.3:1.

Agitation is started, oxygen feed (at a rate of 200 cc/min) is begun and the reaction mixture is heated to 67° C. It is then maintained at this temperature for the time periods shown in the table, after which a sample is analyzed by vapor phase chromatography to determine ALA conversion.

The reaction is discontinued, cooled to room temperature, and the reaction mixture separates into two layers. The aqueous layer is drawn off and extracted with benzene. The combined extracts and the benzene layer are analyzed for palladium content. Selectivity to 2,5-hexanedione is determined by a quantitative analysis of the benzene layers by vapor phase chromatography. Using this procedure, results are as shown in the table below.

The HDO product can be isolated by distilling the benzene at atmospheric pressure and distilling the residue under vacuum. 2,5-Hexanedione is a colorless liquid having a boiling point of 73.5° C/15 mm Hg.

EXAMPLES 6-9

The above experiments are repeated by recycling the aqueous oxidant solution reclaimed along with a fresh charge of ALA and solvent. Each reaction is run until VPC analysis shows at least 90% ALA conversion. Results are as follows:

TABLE 3

| Example | Reaction Time (hours) | % ALA Conversion | % HDO Selectivity | % HDO Yield | Pd Loss cent/lb HDO |
|---|---|---|---|---|---|
| 6 | 1.9 | 94 | 86 | 81 | 330 |
| 7 | 1.7 | 96 | 91 | 87 | 189 |
| 8 | 1.8 | 94 | 86 | 81 | 19 |
| 9 | 1.8 | 92 | 86 | 80 | 2 |

The foregoing results indicate that repetition of the process with recycling of the catalyst solution of this invention improves both selectivity and overall yields of product, particularly for catalysts containing the highest Cu/Pd mole ratios. At the same time, minimum palladium losses are maintained and may, in some instances, be even further reduced. Recycling and use of the catalyst solutions containing the Cu/Pd and Cu/ALA mole ratios taught by the prior Japanese patent teaching provide neither reduced palladium losses nor significant improvements in selectivity.

EXAMPLE 10

The process of this invention is conducted in a semi-continuous manner as follows:

Using the equipment as outlined in Example 1A, a run is made in which the aqueous solution is recycled to the reactor without exhaustive extraction of the HDO after each cycle. The aqueous solution is composed of 20.0 g (0.149 mole) of cupric chloride, 10.0 g (0.100

TABLE 2

| Example | Mole Ratio Cu/Pd | Mole Ratio Cu/ALA | R.T. hours | % ALA Conversion | % HDO Selectivity | % HDO Yield | Pd Loss cent/lb HDO |
|---|---|---|---|---|---|---|---|
| 2 | 13 | 0.73 | 2.0 | 98 | 85 | 84 | 288 |
| 3 | 17 | 0.91 | 2.0 | 100 | 83 | 79 | 190 |
| 4 | 25 | 1.3 | 2.5 | 95 | 83 | 79 | 24 |
| 5 | 44 | 2.4 | 2.7 | 95 | 70 | 69 | 2 |

As these results indicate, palladium losses are least significant when the oxidation process is conducted employing Cu/Pd mole ratios above 20:1 and Cu/ALA mole ratios greater than 1 (Examples 4 and 5), according to the process of this invention. It is to be noted that although overall product yields per batch may be somewhat reduced employing such mole ratios, these losses in selectivity are more than compensated for by the substantial savings realized through minimal losses of the expensive palladium catalyst component.

mole) of cuprous chloride, 0.80 g (0.0453 mole) of palladium chloride, 100 cc of water, and 5 cc HDO. The copper:palladium ratio is 55:1. Twenty cc (0.163 mole) of ALA and 150 cc of benzene are used for each cycle. The copper:ALA ratio is 1.5:1. The reaction temperature is 67° C and the oxygen feed rate is 400 cc/min.

At the end of each cycle, the reaction mixture is cooled to 30° C and the benzene layer is drawn off and analyzed for ALA, HDO, and palladium. A fresh charge of ALA and benzene is added to the aqueous layer in the reactor and the solution is heated to reflux again. Results of several cycles are as follows:

TABLE 4

| Cycle | Reaction Time (hours) | % ALA Conversion | % HDO Selectivity | % HDO Yield | Pd Loss cent/lb HDO |
|---|---|---|---|---|---|
| 1 | 1.5 | 96 | 77 | 74 | 12.5 |
| 2 | 1.5 | 88 | 92 | 81 | 19.0 |
| 3 | 2.8 | 86 | 85 | 73 | 19.0 |
| 4 | 2.3 | 85 | 89 | 76 | 5.8 |
| 5 | 2.5 | 87 | 85 | 74 | 4.2 |
| 6 | 3.0 | 89 | 82 | 73 | 6.0 |
| 7 | 2.5 | 86 | 87 | 75 | 4.0 |
| 8 | 2.5 | 87 | 87 | 76 | 3.7 |
| 9 | 2.3 | 87 | 85 | 74 | 5.6 |

TABLE 4-continued

| Cycle | Reaction Time (hours) | % ALA Conversion | % HDO Selectivity | % HDO Yield | Pd Loss cent/lb HDO |
|---|---|---|---|---|---|
| 10 | 2.5 | 86 | 85 | 73 | 7.1 |

I claim:

1. In a process wherein allylacetone is oxidized to 2,5-hexanedione in a mixed solvent system containing per part of water, by volume, from one to two parts benzene by contacting said allylacetone with palladium chloride catalyst in the presence of copper chloride and oxygen, the improvement which comprises conducting the reaction without adding hydrochloric acid and employing from 25 to 55 moles of copper chloride per mole of palladium chloride, the amount of copper chloride being sufficient to provide a molar ratio of said copper chloride to allylacetone of 1.3 – 2.4, whereby greater than 80% allylacetone conversion is effected with at least 70% selectivity to 2,5-hexanedione and with minimal losses of the palladium catalyst.

2. The process of claim 1 wherein from 25 to 44 moles of copper chloride are employed per mole of palladium chloride.

3. The process of claim 1 wherein cupric chloride is employed.

4. The process of claim 1 wherein a mixture of cupric chloride and cuprous chloride is employed.

5. The process of claim 1 wherein oxygen is fed at a minimum rate of 50 cc/min/liter of aqueous catalyst solution.

6. The process of claim 1 which is conducted at a temperature of 35°–100° C for a time period ranging from 30 minutes to 6 hours.

* * * * *